US010070816B2

(12) United States Patent
Cowley et al.

(10) Patent No.: US 10,070,816 B2
(45) Date of Patent: Sep. 11, 2018

(54) ORTHOTIC SENSOR DEVICE

(71) Applicant: Intel Corporation, Santa Clara, CA (US)

(72) Inventors: Nicholas P. Cowley, Wroughton (GB); Ruchir Saraswat, Swindon (GB); Richard J. Goldman, Cirencester (GB)

(73) Assignee: Intel Corporation, Santa Clara, CA (US)

( * ) Notice: Subject to any disclaimer, the term of this patent is extended or adjusted under 35 U.S.C. 154(b) by 666 days.

(21) Appl. No.: 14/481,375

(22) Filed: Sep. 9, 2014

(65) Prior Publication Data

US 2016/0066818 A1 Mar. 10, 2016

(51) Int. Cl.
*A61B 5/00* (2006.01)
*A61B 5/103* (2006.01)
(Continued)

(52) U.S. Cl.
CPC .......... *A61B 5/6807* (2013.01); *A61B 5/1038* (2013.01); *A43B 3/0005* (2013.01); *A61B 5/112* (2013.01); *A61B 2560/0214* (2013.01); *A61B 2562/028* (2013.01); *A61B 2562/0247* (2013.01); *A61B 2562/12* (2013.01);
(Continued)

(58) Field of Classification Search
CPC ................ A61B 5/1036; A61B 5/6807; A61B 2562/0247
See application file for complete search history.

(56) References Cited

U.S. PATENT DOCUMENTS

| 6,454,708 B1* | 9/2002 | Ferguson | ........... A61B 5/02055 128/903 |
| 8,384,551 B2* | 2/2013 | Ross | .................... A43B 3/0005 340/573.1 |

(Continued)

FOREIGN PATENT DOCUMENTS

| JP | 2008-546500 A | 12/2008 |
| JP | 2013-233269 A | 11/2013 |

(Continued)

OTHER PUBLICATIONS

Taiwan Office Action and Search Report dated May 12, 2016, issued in corresponding Taiwan Patent Application No. 104125102, 13 pages.

(Continued)

*Primary Examiner* — Sean Dougherty
(74) *Attorney, Agent, or Firm* — Schwabe, Williamson & Wyatt, P.C.

(57) ABSTRACT

Embodiments of the present disclosure provide techniques and configurations for an orthotic device. In one instance, the device may include an orthotic device body and at least two sensors spatially disposed inside the orthotic device body. A first sensor may provide a first output responsive to pressure resulting from application of mechanical force to the orthotic device body. A second sensor may provide a second output responsive to flexing resulting from the application of mechanical force to the orthotic device body. The device may also include a control unit communicatively coupled with the sensors to receive and process the outputs provided by the sensors in response to pressure and flexing. Other embodiments may be described and/or claimed.

20 Claims, 7 Drawing Sheets

(51) Int. Cl.
*A43B 3/00* (2006.01)
*A61B 5/11* (2006.01)

(52) U.S. Cl.
CPC ... *A61B 2562/164* (2013.01); *A61B 2562/166* (2013.01); *A61B 2562/187* (2013.01)

(56) References Cited

U.S. PATENT DOCUMENTS

| | | | | |
|---|---|---|---|---|
| 8,893,561 | B2* | 11/2014 | Gorjanc | G01L 1/146 |
| | | | | 73/862.046 |
| 9,215,905 | B2* | 12/2015 | Tseng | A43B 7/02 |
| 9,453,772 | B2* | 9/2016 | Ross | A43B 3/0005 |
| 9,502,638 | B2* | 11/2016 | McAlpine | H01L 41/314 |
| 9,510,776 | B2* | 12/2016 | Lee | A61B 5/6829 |
| 9,629,558 | B2* | 4/2017 | Yuen | A61B 5/0205 |
| 9,743,861 | B2* | 8/2017 | Giedwoyn | A61B 5/112 |
| 9,756,895 | B2* | 9/2017 | Rice | G01L 1/20 |
| 9,790,928 | B2* | 10/2017 | Wang | F03G 5/06 |
| 2010/0090477 | A1* | 4/2010 | Keating | F03G 7/08 |
| | | | | 290/1 R |
| 2011/0033830 | A1* | 2/2011 | Cherian | G09B 5/02 |
| | | | | 434/236 |
| 2011/0275956 | A1* | 11/2011 | Son | A43B 3/0005 |
| | | | | 600/592 |
| 2013/0000156 | A1 | 1/2013 | Andoh et al. | |
| 2014/0260689 | A1* | 9/2014 | Walker | G01L 1/2206 |
| | | | | 73/862.625 |
| 2015/0253210 | A1* | 9/2015 | Ashby | A61B 5/6807 |
| | | | | 702/41 |

FOREIGN PATENT DOCUMENTS

| | | |
|---|---|---|
| JP | 2014-505574 A | 3/2014 |
| KR | 10-1511036 B1 | 4/2015 |
| TW | 201312921 A | 3/2013 |
| WO | 01/36051 A2 | 5/2001 |
| WO | 2001036051 A2 | 5/2001 |
| WO | 2012112930 A1 | 8/2012 |
| WO | 2011114977 A1 | 6/2013 |

OTHER PUBLICATIONS

International Search Report Report and Written Opinion dated Nov. 17, 2015, issued in corresponding International Application No. PCT/US2015/044082, filed Aug. 6, 2015, 14 pages.
Gullapalli, et al., "Flexible Piezoelectric ZnO-Paper nanocomposite Strain Sensor," Wiley-VCH Verlag GmbH, Small 2010, No. 15, 1641-1646, Jul. 7, 2010.
Sinha, et al., "Ultra Thin ALN Piezoelectric Nano-Actuators," Transducers 2009, Denver, CO, Jun. 21-25, 2009, 4 pages.
Murata Manufacturing Co., Ltd., "Murata Introduces World's First Ultra-Thin Waterproof Piezoelectric Speaker," Murata Newsroom, Jun. 8, 2010, 2 pages.
Telegraph Media Group Ltd., "Korean Researchers Develop Flexible Battery," The Telegraph, Sep. 11, 2014, 1 page.
International Preliminary Report on Palatability dated Mar. 23, 2017, issued in corresponding International Application No. PCT/US2015/044082, filed Aug. 6, 2015, 10 pages.
Notice of Reason(s) for Rejection dated Feb. 27, 2018, issued in related Japanese Patent Application No. 2017-513243, 9 pages.

* cited by examiner

ORTHOTIC SENSOR DEVICE

FIELD

Embodiments of the present disclosure generally relate to the field of sensor devices, and more particularly, to orthotic sensor devices to measure pressure and flexing resulting from application of mechanical force to footwear.

BACKGROUND

There exist some devices that may be associated with footwear to provide diagnostic data related to foot load imbalance, and measure pressure provided by a user's foot to the footwear. Similarly, some gaming devices are known that may provide foot pressure measurements. However, such devices are limited to measuring pressure and may typically provide static pressure measurements. Furthermore, local power sources used, for example, in footwear-associated devices may limit the devices' usage. Also, such devices may require an external physical connection to a data processing device. Such external physical connection, when worn by a user, may encumber the user and impede or restrict his or her movement.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example and not by way of limitation in the figures of the accompanying drawings.

DETAILED DESCRIPTION

Figure 1:
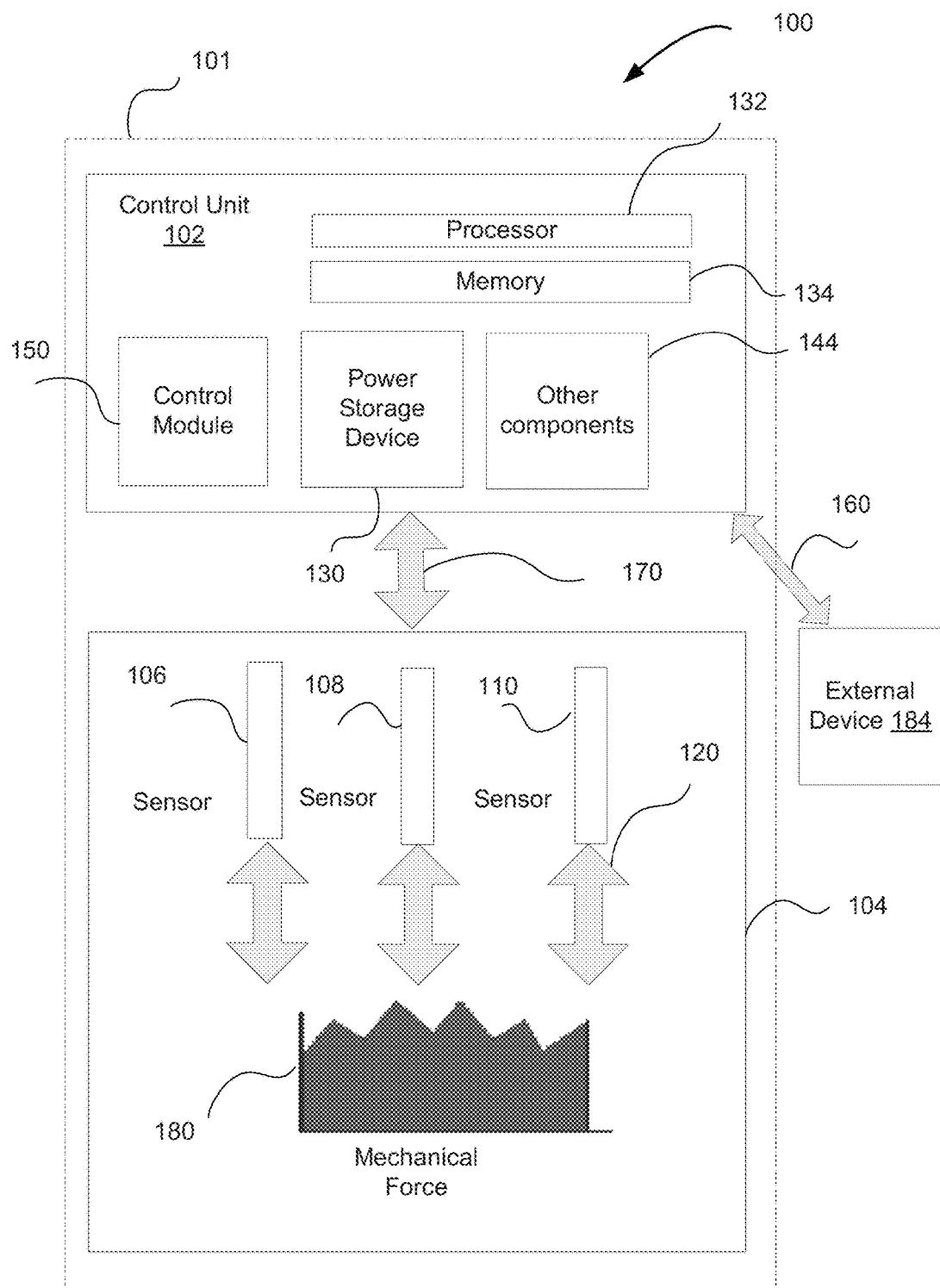
FIG. 1 is a block diagram of an example orthotic device in accordance with some embodiments of the present disclosure.

Embodiments of the present disclosure include techniques and configurations for an orthotic sensor device, in particular, a device configured to provide measurements of pressure and flexing resulting from mechanical force applied to the device, e.g., by a user's foot during perambulation. In accordance with embodiments, the orthotic device may include an orthotic device body and at least two sensors spatially disposed inside the orthotic device body. A first sensor may be configured to provide a first output responsive to pressure resulting from application of mechanical force to the orthotic device body. A second sensor may be configured to provide a second output responsive to flexing resulting from the application of mechanical force to the orthotic device body.

The device may include a control unit communicatively coupled with the two sensors inside the orthotic device body to receive and process the first and second outputs. Processing of the first and second outputs may include extraction of electric power from the outputs for electrical power harvesting, which may occur locally, e.g., with a power storage device disposed inside the device body, or externally.

In the following detailed description, reference is made to the accompanying drawings that form a part thereof, wherein like numerals designate like parts throughout, and in which are shown by way of illustration embodiments in which the subject matter of the present disclosure may be practiced. It is to be understood that other embodiments may be utilized and structural or logical changes may be made without departing from the scope of the present disclosure. Therefore, the following detailed description is not to be taken in a limiting sense, and the scope of embodiments is defined by the appended claims and their equivalents.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B, and C).

The description may use perspective-based descriptions such as top/bottom, in/out, over/under, and the like. Such descriptions are merely used to facilitate the discussion and are not intended to restrict the application of embodiments described herein to any particular orientation.

The description may use the phrases "in an embodiment," or "in embodiments," which may each refer to one or more of the same or different embodiments. Furthermore, the terms "comprising," "including," "having," and the like, as used with respect to embodiments of the present disclosure, are synonymous.

The term "coupled with," along with its derivatives, may be used herein. "Coupled" may mean one or more of the following. "Coupled" may mean that two or more elements are in direct physical, electrical, or optical contact. However, "coupled" may also mean that two or more elements indirectly contact each other, but yet still cooperate or interact with each other, and may mean that one or more other elements are coupled or connected between the elements that are said to be coupled with each other.

FIG. 1 is a block diagram of an example orthotic device 100 in accordance with some embodiments of the present disclosure. The orthotic device 100 may be used in various implementations. For example, the orthotic device 100 may comprise a wearable device configured to provide sensor measurement of data related to a user's activities, such as walking, running, jumping, or the like. More specifically, the orthotic device 100 may comprise one or more (in some embodiments, two or more) sensors to measure data related to pressure and/or flexing that may result from application of mechanical force to the orthotic device, such as mechanical force applied by a user's foot to the orthotic device. In embodiments, the orthotic device may be configured to be used with an article of footwear. For example, the orthotic device 100 may be insertable or embeddable in the article of footwear, or otherwise built into the article of footwear.

In some embodiments, the orthotic device 100 may comprise an orthotic device body 101 that may comprise thermoplastics, polyethylene foam, cork, acrylic, polypropylene, composite carbon fiber, or other material commonly used to manufacture orthotic devices. The orthotic device body 101 of the orthotic device 100 may include (e.g., encapsulate) a control unit 102 and a sensor unit 104. One skilled in the art will appreciate that the control unit 102 and sensor unit 104 may not necessarily be physically separate entities. The designation of these components of the orthotic device 100 is supposed to underline functional differences between the control unit 102 and sensor unit 104, rather than imply their physical location or placement inside the orthotic device body 101. For example, the control unit 102 may be configured to manage the sensor unit 104. The control unit 102 may be communicatively coupled 170 with the sensor unit 104.

The sensor unit 104 may include one or more sensors 106, 108, 110 (in some embodiments, a sensor array) that may be spatially disposed inside the orthotic device body 101, as will be described in greater detail in reference to FIGS. 2 and 4-6. The sensors 106, 108, 110 are shown in FIG. 1 for illustrative purposes only; it will be appreciated that any number of sensors (e.g., one or more) may be used in the sensor unit 104. The sensors 106, 108, 110 may be operatively coupled 120 with a process 180 that applies mechanical force and configured to measure data indicative of the process 180.

Generally, the process 180 may be any type of digital or analog process, continuous or periodic, that may be defined in measureable physical quantities, which may be convertible into a signal readable by a respective sensing device. For example, the process 180 may include, but may not be limited to, various types of motion, temperature, gravity, humidity, moisture, vibration, electrical fields, biometric processes, and other physical aspects. The measurable data indicative of a process may include different physical characteristics and parameters. Accordingly, sensors 106, 108, 110 may include different types of sensors, including, but not limited to, accelerometers, gyroscopes, barometers, infrared proximity sensors, visible light sensors, transducers, actuators, and the like. For purposes of this disclosure, the process 180 may include application of mechanical force (e.g., applied by a user's foot) to footwear including the orthotic device 100. Accordingly, the mechanical force may be considered to be applied to the orthotic device body 101 by a user's foot substantially placed on the orthotic device body disposed inside the footwear, e.g., inside or around a sole of the footwear.

In some embodiments, the sensors 106, 108, 110 may include at least one sensor (e.g., 106) to provide a first output responsive to pressure resulting from application of mechanical force to the orthotic device body 101. For example, the sensor 106 may provide information about real time (e.g., dynamic) balance or weight (load) distribution across footwear that includes the orthotic device 100 resulting from the user's foot movement, e.g., during perambulation.

The sensors 106, 108, 110 may include at least one sensor (e.g., 108) to provide a second output responsive to flexing resulting from the application of mechanical force 180 to the orthotic device body 101. For example, the sensor 108 may provide information on bending moment applied to the orthotic device body 101. Such measurements may be used, for example, in medical diagnostics (e.g., gait correction) or data gathering under real usage conditions, such as walking, running, or other physical activities involving perambulation, as well as in the gaming industry and the like. Such diagnostic information may be used, for example, by orthopedic consultants, physiotherapists, and other physicians for the treatment of conditions arising from, for example, ankle displacement, leg length imbalance, hip displacement, and the like.

In some embodiments, sensors 106, 108, 110 may comprise piezoelectric devices. The amount of electric power produced by a piezoelectric device may be directly proportional to the pressure or flexing applied to a material. Accordingly, using piezoelectric devices as sensors 106, 108, 110 may enable harvesting of electrical power provided by the sensors' output, in combination with providing pressure and flexing measurements.

Some piezoelectric materials such as macro fiber composites (MFC) and advanced polymer structures may enable a provision of flexible piezoelectric sensors 106, 108, 110. MFC devices may have a desired thickness (e.g., may be ultra-thin) and may be suitable to encapsulation in materials commonly used to manufacture orthotic devices.

The control unit 102 may be configured to process data outputs provided by the sensors 106, 108, 110. For example, the control unit 102 may receive electric signals generated by the sensors 106, 108, 110, and generate an output related to the load distribution and flexing, which may be passed via connection 160 for further processing, for example, to an external computing device 184. In some embodiments, such external computing device 184 may comprise a wearable monitoring device.

More specifically, the control unit 102 may include a processor 132 and memory 134 having instructions (e.g., compiled in a control module 150) that, when executed on the processor 132, may cause the processor 132 to perform processing of data outputs provided by the sensors 106, 108, 110 and storing and/or passing on of the processed information.

The control module 150 may be implemented as a software component stored, e.g., in the memory 134 and configured to execute on the processor 132. In some embodiments, the control module 150 may be implemented as a combination of software and hardware components. In some embodiments, the control module 150 may include a hardware implementation.

The processor 132 may be packaged together with computational logic, e.g., implemented by the control module 150, and configured to practice aspects of embodiments described herein, such as sensor output processing to form a System in Package (SiP) or a System on Chip (SoC). The processor 132 may include any type of processors, such as a central processing unit (CPU), a microprocessor, and the like. The processor 132 may be implemented as an integrated circuit having multi-cores, e.g., a multi-core microprocessor. The memory 134 may include a mass storage device that may be temporal and/or persistent storage of any type, including, but not limited to, volatile and non-volatile memory, optical, magnetic, and/or solid state mass storage, and so forth. Volatile memory may include, but is not limited to, static and/or dynamic random-access memory. Non-volatile memory may include, but is not limited to, electrically erasable programmable read-only memory, phase change memory, resistive memory, and so forth. The memory 134 may be used for storage of the processed outputs from the sensors 106, 108, 110.

The control unit 102 may include a power storage device 130. The power storage device 130 may be configured to supply power to at least some (or all) of the sensors 106, 108, 110, and to the control unit 102, and may be operated by the control unit 102. In some embodiments, the power storage device 130 may comprise a battery (or capacitor) disposed inside the orthotic device body 101 and coupled with the control unit 102 via a wired connection (not shown).

As discussed above, the sensors 106, 108, 110 may comprise piezoelectric devices. The control unit 102 may be configured to process the outputs provided by the piezoelectric sensors 106, 108, 110 to rectify the outputs (e.g., extract electric power signals from the outputs) and pass the extracted electric power signals to the power storage device 130, or to an external power storage (e.g., included in the external computing device 184) via connection 160, which may be a wireless or wired connection. In some embodiments, the power storage device may further comprise one of the piezoelectric sensors 106, 108, 110 configured to supply power to other sensors and to the control unit 102.

The control unit 102 may include other components 144 necessary for the functioning of the control unit 102. The processing functions of the control unit 102 may include a means for measuring the magnitude and rate of change of the output of each sensor. For example, the sensors may interface with an analog-to-digital converter (ADC) that may convert the analogue output signal to a digital signal, which may be processed by the control unit 102 or passed by the control unit 102 to an external computing device for further processing.

Accordingly, the other components 144 may be configured to provide the wireless connection 160 and include, for example, a transceiver and other communication means as necessary, such as one or more communication interfaces configured to facilitate information exchange between the control unit 102 and external computing device 184. The communication interfaces may include communication chips (not shown) that may be configured to operate in accordance with communication protocols known in the art, such as wireless or wired communication protocols.

Figure 2:
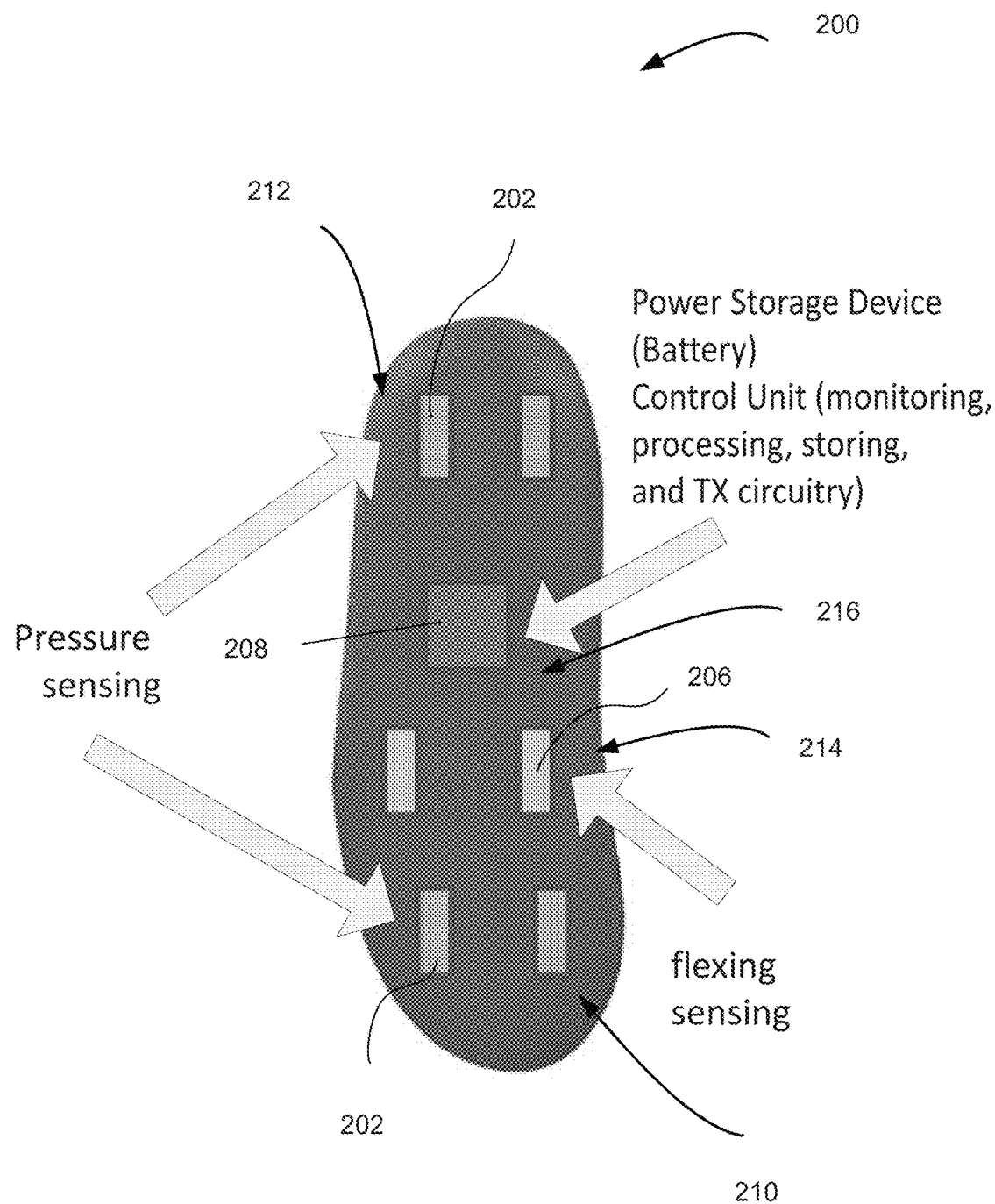
FIG. 2 is a schematic representation of an example spatial distribution of pressure and flexing sensors inside an orthotic device placed in footwear, according to some embodiments.

FIG. 2 is a schematic representation of an example spatial distribution of pressure and flexing sensors inside an orthotic device placed in footwear, according to some embodiments. In order to provide a desired precision level of measurements, multiple sensors may be spatially disposed around different areas of an orthotic device body 200 (and thus around different areas of the respective sole of footwear inside which the orthotic device is placed), corresponding to different areas of a user's foot. For example, pressure applied by a person's foot to footwear during perambulation may be detected in areas around a ball of the foot or a heel. Flexing (e.g., bending moment) applied by a person's foot to footwear during perambulation may be detected in areas around a middle of the foot.

Accordingly, as shown in FIG. 2, pressure sensors 202 may be disposed in a first area of the orthotic device body 200 that may correspond to a ball area 210 or a heel area 212 of a user's foot. Flexing sensors 206 may be disposed in a second area of the orthotic device body 200 that may correspond to a rear 214 of the ball area 210 of the user's foot. The associated processing components 208 (e.g., control unit 102 including processor 132, memory 134, power storage device 130, and other components 144 such as transceiver blocks) may be, in this illustrative example, placed in an area corresponding to an arch area 216 of the user's foot, which is normally the area with the least load bearing. In some embodiments, for example, with fallen arch syndrome, this area may also include sensor(s) 106, 108, 110 and/or the associated processing components. In some embodiments, the associated processing components may be located in other areas of the orthotic device body 200. In some embodiments, sensor and processing functions may be customized based on an individual's requirements.

Figure 3:
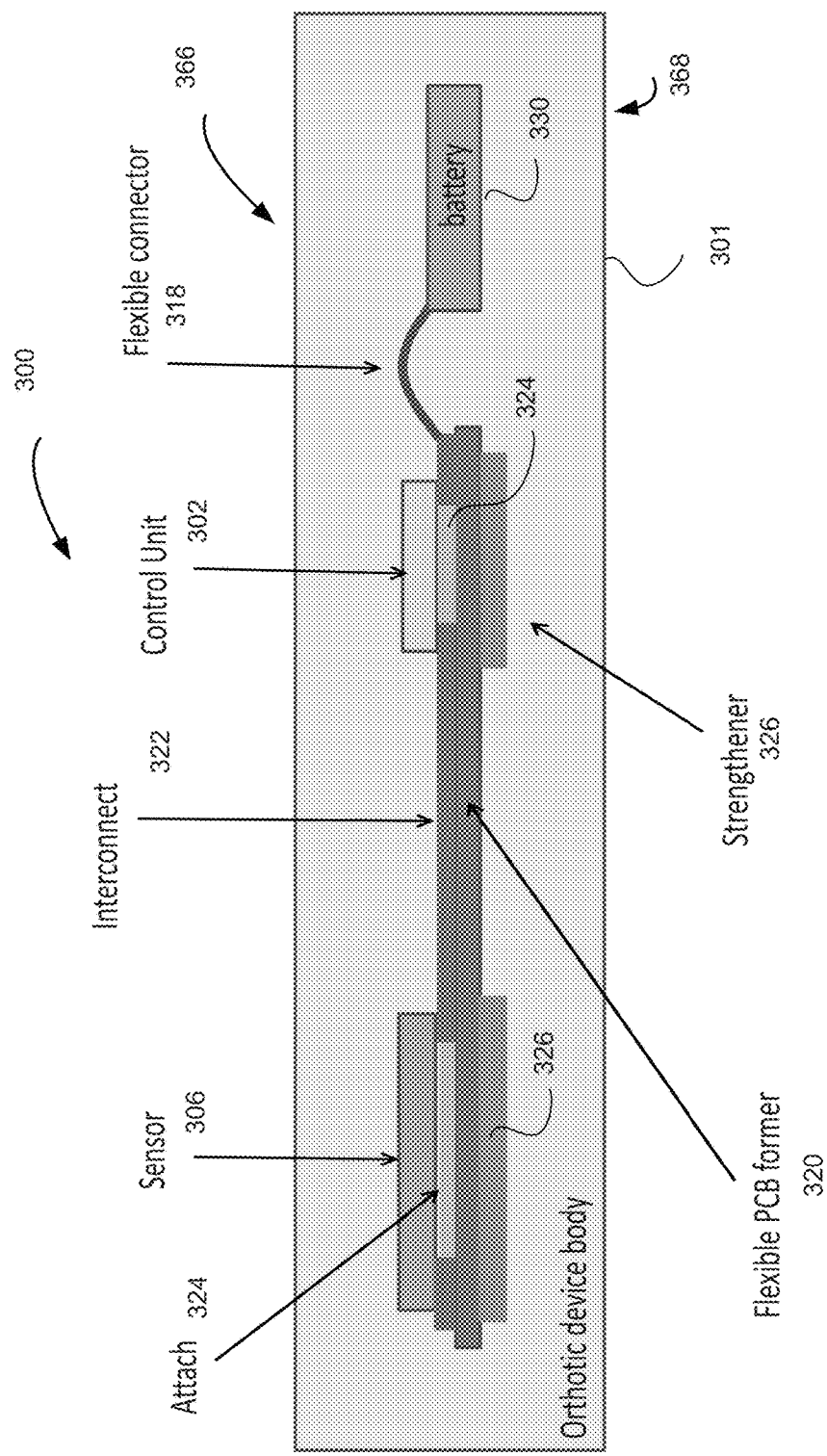
FIG. 3 is a schematic diagram illustrating a cross-section of an example embodiment of an orthotic device, according to some embodiments.

FIG. 3 is a schematic diagram illustrating a cross-section of an example embodiment of an orthotic device 300, according to some embodiments. As discussed in reference to FIG. 1, the orthotic device 300 may include an orthotic device body 301. The orthotic device body 301 may be fabricated from thermoplastic (e.g., semi-rigid thermoplastic), polyethylene foam, cork, acrylic, polypropylene, composite carbon fiber, or other material commonly used to manufacture orthotic devices. The orthotic device body 301 may include (e.g., encapsulate) the orthotic device components. In some embodiments, the orthotic device 300 may be formed by injection of the orthotic device body material around the device components or by "sandwiching" the components between an upper section 366 and lower section 368 of the orthotic device body 301. In some embodiments, the thickness of the orthotic device body 301 may be approximately between 3 and 6 mm. In other embodiments, the thickness may be determined by medical or other requirements, for example to address gait correction or other medical problems.

As discussed in reference to FIGS. 1-2, the orthotic device 300 may include one or more (in some instances, two or more) sensors 306, a control unit 302 (having a processor, a memory, and other components), and a power storage device (battery or capacitor, e.g., super capacitor) 330 coupled with the control unit 302. In some embodiments, the power storage device 330 may have a thickness of approximately between 0.2 and 0.5 mm.

Some of the sensors 306 and control unit 302 components (e.g., processor and/or memory) may be attached to a flexible printed circuit board (PCB) (e.g., encased in a flexible former) 320. In some embodiments, the flexible PCB (former) 320 may have a thickness of about 0.2 mm. The flexible PCB (former) 320 may include a flexible electrical interconnect 322. In some embodiments, the interconnect 322 may comprise copper, for example. In general, the interconnect 322 may be implemented as a metal deposition on the flexible PCB (former) 320. In some embodiments, the interconnect 322 may be implemented as embedded wire connections.

Some of the device components (e.g., sensors 306 and control unit 302) may be attached to the flexible PCB (former) 320 by flexible adhesive (attach) 324, so that electrical contact for the sensors 306 and control unit 302 may be maintained with the electrical interconnect 322. In some embodiments, the battery 330 may be located separately from the flexible PCB (former) 320 and connected to the device components via a flexible connector 318, as shown. There may be optional strengthening material 326 attached to at least some portions of the flexible PCB (former) 320 (e.g., in the sensor 306 area or control unit 302 area) to prevent over-flexing of contacts and delamination.

The sensors 306 may comprise piezoelectric devices and have widths around 0.1 to 0.3 mm, and the control unit 302 (e.g., implemented as a processor chip) may have a thickness of about 0.1 mm. The antenna for the transceiver (not shown) may be formed, e.g., by patterning on the flexible PCB (former) 320. Similarly, a coil that may be used for wireless transfer of electric power to an external power storage device (not shown) may also be formed by patterning on the flexible PCB (former) 320.

Figure 4:
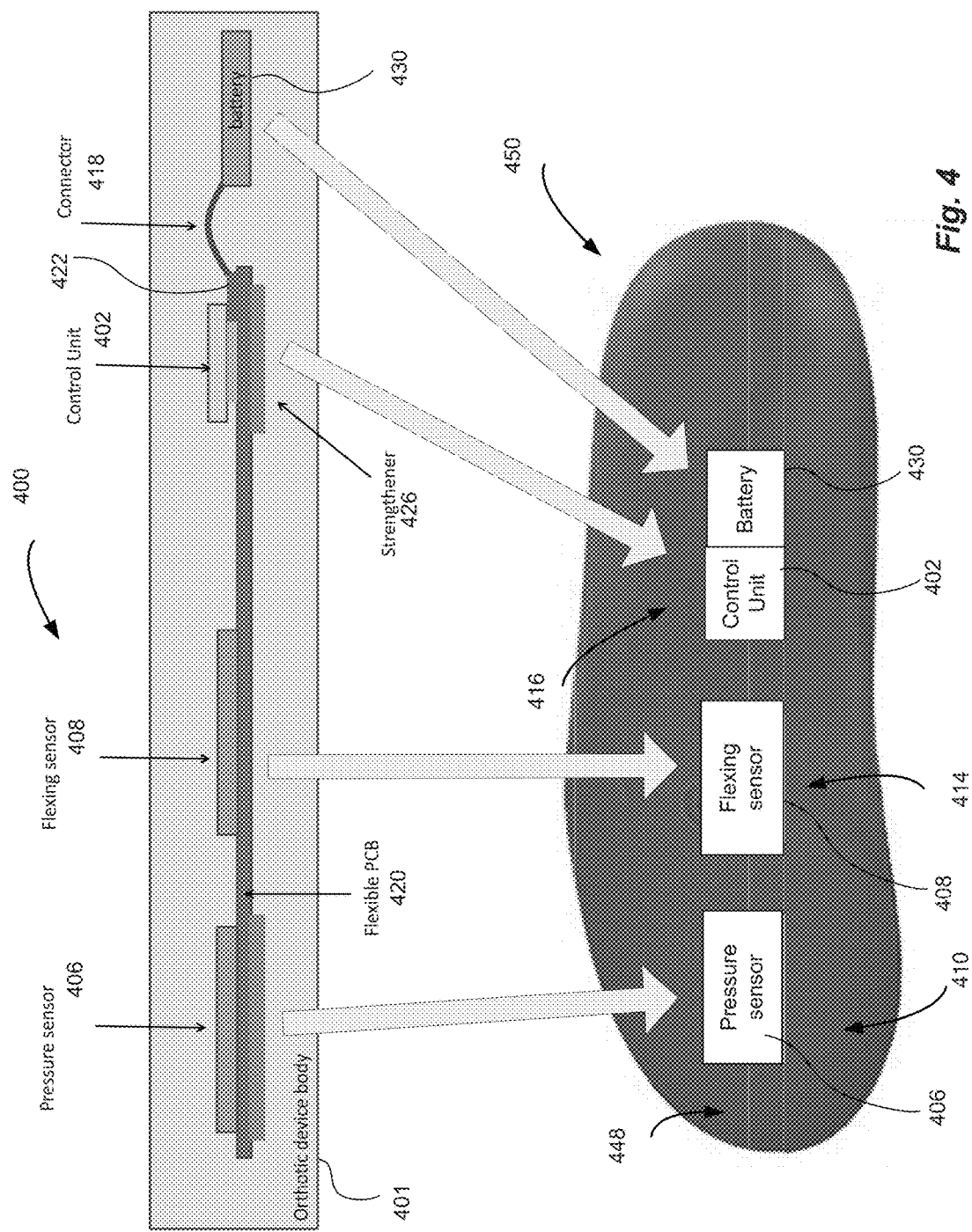
FIG. 4 is a schematic diagram illustrating a cross-section of another example embodiment of an orthotic device, also showing spatial placement of some device components, according to some embodiments.

FIG. 4 is a schematic diagram illustrating a cross-section of another example embodiment of an orthotic device 400, also showing spatial placement of some device components in a back view 450 of the orthotic device 400, according to some embodiments. FIG. 4 is expanded to include a pressure sensor 406 and flexing sensor 408 and to indicate how these may be located within the orthotic device 400 to provide feedback on the different types of movement and forces exerted across the foot. As described in reference to FIG. 3, the orthotic device 400 may include an orthotic device body 401 encapsulating at least some of the device components, such as pressure sensor 406, flexing sensor 408, control unit 402, and battery 430, that may be connected to the device components via a flexible connector 418. The orthotic device 400 may include flexible PCB (former) 420, on which some of the device components may be disposed as described in reference to FIG. 3. The orthotic device 400 may include interconnect 422 and strengthener 426, as shown.

As shown, the pressure sensor 406 may be placed around an area 410 corresponding to the ball of the user's foot, and the flexing sensor 408 may be placed around an area 414 corresponding to a rear of the ball of the user's foot. The control unit 402 and the battery 430 may be placed in an area 416 corresponding to an arch of the user's foot. One skilled in the art will appreciate that the described embodiment is not meant to restrict the placement of certain sensor types to a given area. For example, a flexing sensor (similar to 408) may be placed around (e.g., in front of) the pressure sensor 406, e.g., to provide feedback on the bending moment around a toe area 448.

While FIGS. 3-4 illustrate a flexible PCB (former) as carrying the sensors, in general, the flexible PCB (former) may or may not be included in one or more of the areas within the orthotic device 300 or 400.

In some embodiments the sensors of an orthotic device, such as piezoelectric sensors, may be used for the purpose of energy harvesting, in which case the output of the sensors may be principally used for extracting electric power signals. In some embodiments, the sensor output may also be used to determine the orientation of the foot to maximize energy transfer to an external device (e.g., external device 184 of FIG. 1), which may be located elsewhere, e.g., on the user's body. For example, an external power storage device may be worn around the ankle of the user and the orthotic orientation information may be used to determine the location of the orthotic device with respect to the ankle to maximize electric power transfer to the external device, for example, in the case of wireless transfer of power. In some embodiments, the orthotic device may include a connector, for example, micro-Universal Serial Bus (USB) port, to enable download of stored data, and/or harvested energy to an external device.

Figure 5:
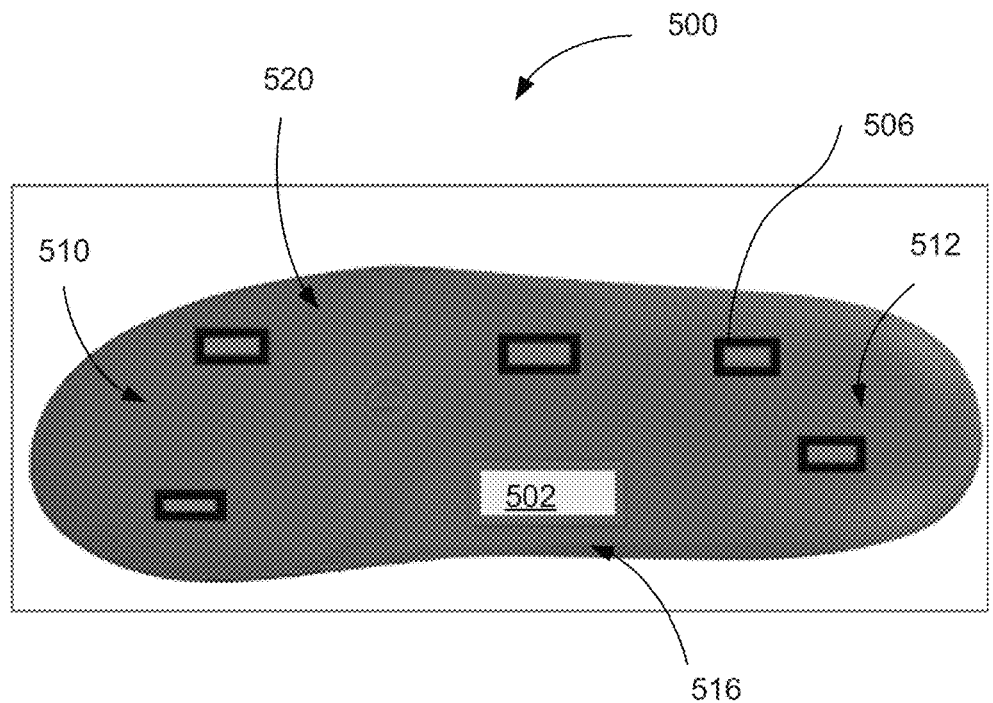
FIGS. 5-6 illustrate schematic representations of example spatial distributions of pressure and flexing sensors inside an orthotic device placed in footwear, according to some embodiments.
Figure 6:
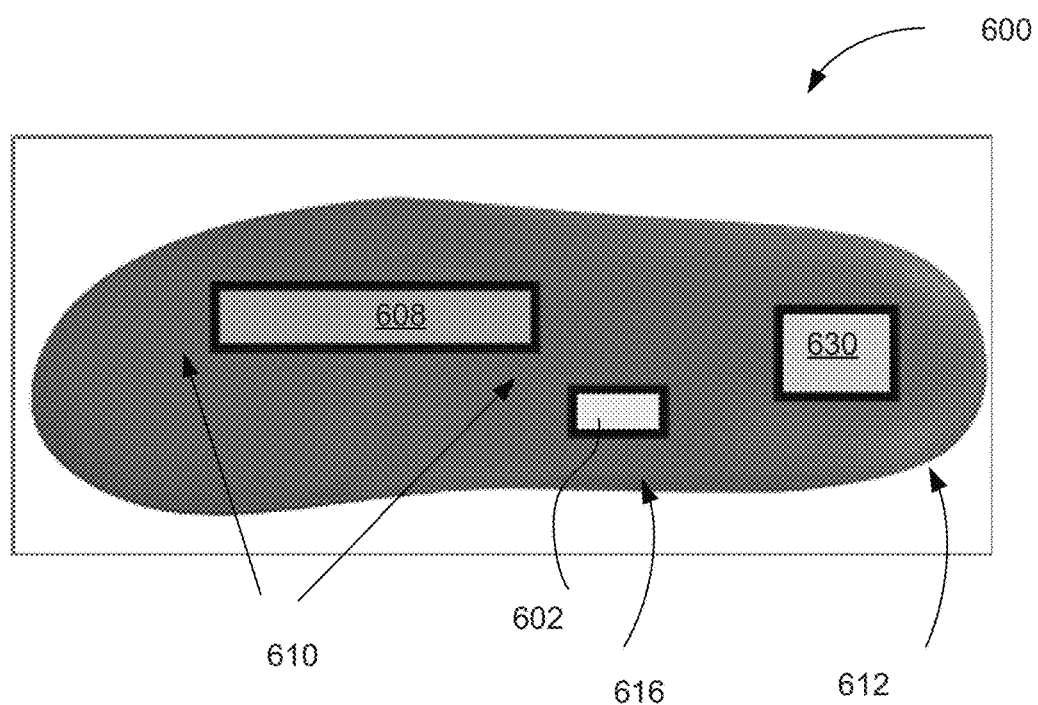

FIGS. 5-6 illustrate schematic representations of example spatial distributions of pressure and flexing sensors inside an orthotic device placed in footwear, according to some embodiments. FIG. 5 illustrates an embodiment of the orthotic device 500 configured to enable pressure measurements and energy harvesting. Accordingly, the orthotic device 500 may include multiple piezoelectric devices (pressure sensors) 506. The pressure sensors 506 may be disposed (e.g., embedded) around a ball of the foot area 510, heel area 512, and outer side of the foot 520. However, the illustrative example of FIG. 5 is not intended as a literal placement of sensors; rather, it is indicative of how a number of sensors may be distributed across the orthotic device to supply information in the distribution of load bearing across the sole of the foot.

The associated processing, charge storage, and transceiver blocks (included in the control unit 502) may be placed in an arch area 516 of the foot, which is normally the area with the least load bearing. In some embodiments, for example, with fallen arch syndrome, this area may also include sensor(s) and/or the associated processing, charge storage, and transceiver may be otherwise located. For example, sensor and processing functions may be customized based on an individual's requirements.

The processing function may include a means for measuring the magnitude and rate of change of the output of each of the sensors 506. For example, the sensors 506 may interface with an ADC to convert the analog output signal to a digital signal, which may be processed within the control unit 502 or passed by the control unit 502 through, for example, a transceiver to an external device, as discussed in reference to FIG. 2. In addition or as an alternative, some or part of the sensor output may be processed to implement an energy harvesting function (e.g., by extracting and storing electric power signals).

FIG. 6 illustrates an embodiment of the orthotic device 600 configured to enable flexing measurements and energy harvesting. The electric charge to be harvested may be generated through flexing rather than direct pressure. Accordingly, the orthotic device 600 may include a piezoelectric device (flexing sensor) 608 placed across an area of the foot with maximum deflection associated with perambulation, indicated by numeral 610. The battery 630 may be placed around the heel area 612, and the control unit 602 may be placed in an arch area 616. The orthotic device 600 may also include a connector for downloading stored charge or a coil for radio frequency (RF) energy sharing (not shown).

Figure 7:
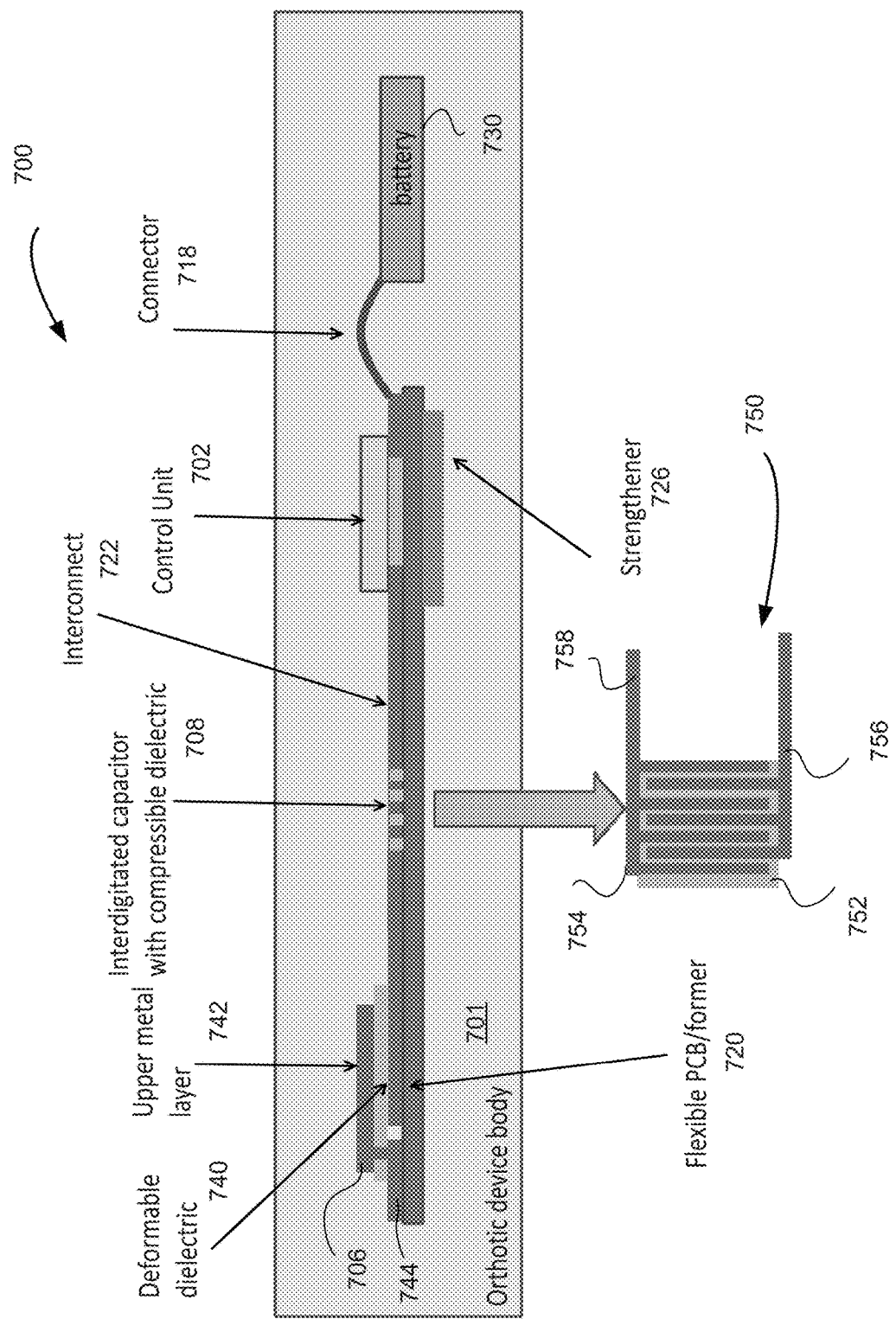
FIG. 7 is a schematic diagram illustrating a cross-section of another example embodiment of an orthotic device, according to some embodiments.

FIG. 7 is a schematic diagram illustrating a cross-section of another example embodiment of an orthotic device 700, according to some embodiments. The orthotic device 700 may include capacitor devices configured to perform pressure and flexing measurements in response to application of mechanical force to footwear containing the orthotic device 700.

Similar to the embodiments described in reference to FIGS. 3-6, the orthotic device 700 may include an orthotic device body 701 encapsulating at least some of the device components, such as pressure sensor 706, flexing sensor 708, and control unit 702. The device 700 may include a battery 730 that may be connected to the device components via a flexible connector 718. The orthotic device 700 may include flexible PCB (former) 720, which may include some of the device components as described in reference to FIGS. 3-4. The orthotic device 700 may include interconnect 722 and strengthener 726, as shown.

The pressure sensor 706 may comprise a capacitor with a deformable dielectric material 740 that is responsive to pressure. The deformable dielectric 740 may be sandwiched between the layers of metal, such as deposited metal (upper layer) 742 and a portion (lower layer) 744.

The flexing sensor 708 may comprise an inter-digitated capacitor with compressible dielectric material that is responsive to the flexing. The structure of the sensor 708 is illustrated in a blown-up view 750. As shown, the sensor 708 may comprise flexing-responsive dielectric material 752 sandwiched between the metal structure 754 comprising two grill-like partially intertwined portions 756 and 758.

While the orthotic device 700 is shown as including both types of capacitor sensors, such as pressure sensor 706 and flexing sensor 708, one skilled in the art will appreciate that an orthotic device similar to one described in reference to FIG. 7 may include multiple capacitor devices responsive to pressure, multiple capacitor devices responsive to flexing, or a combination thereof (as illustrated by FIG. 7).

Figure 8:
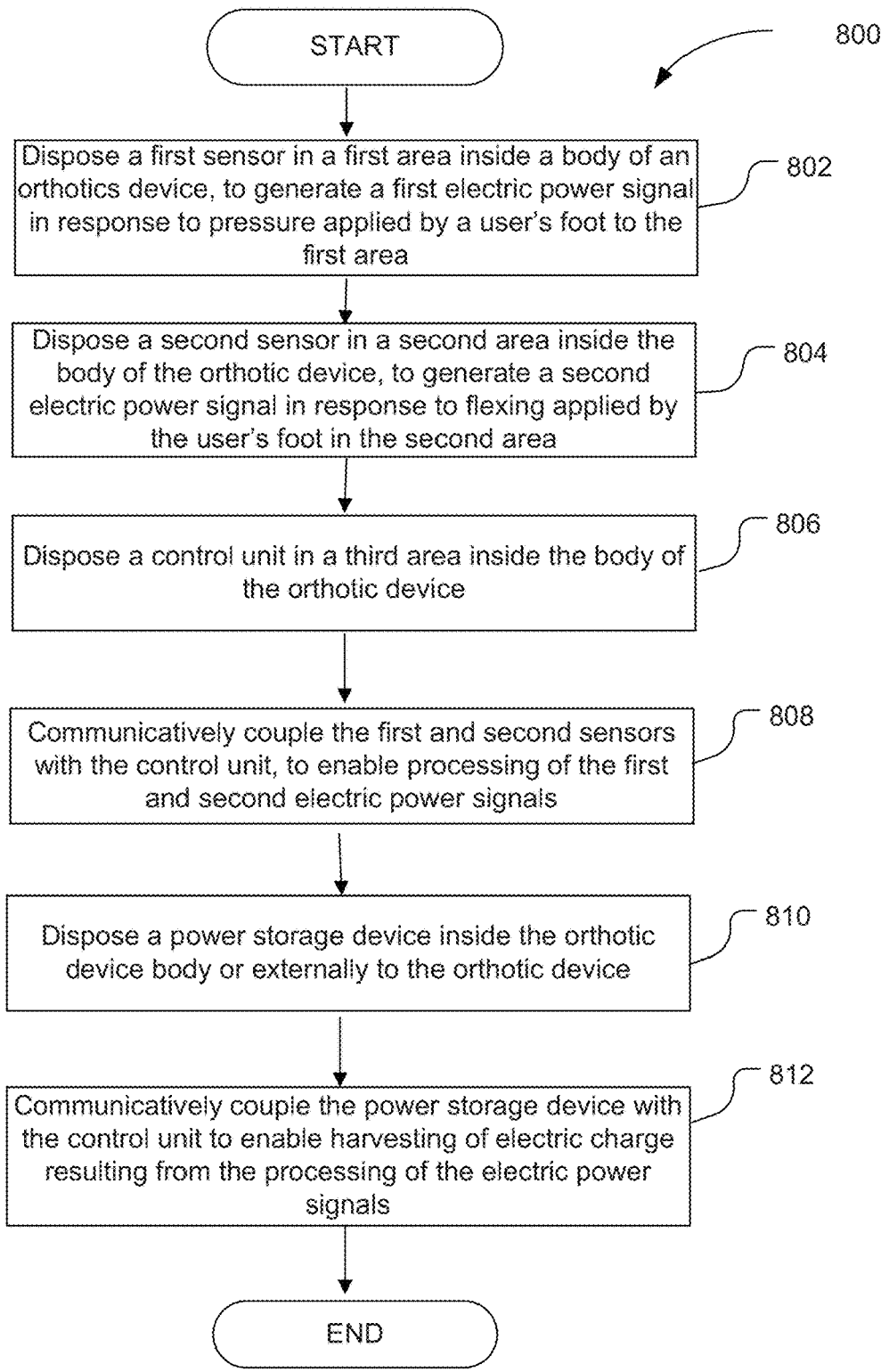
FIG. 8 is a process flow diagram for fabricating an orthotic device, in accordance with some embodiments.

FIG. 8 is a process flow diagram 800 for fabricating an orthotic device, in accordance with some embodiments.

The process 800 may begin at block 802, wherein a first sensor may be disposed in a first area inside a body of an orthotic device. The first sensor may be configured to generate a first electric power signal in response to pressure applied by a user's foot to the first area.

At block 804, a second sensor may be disposed in a second area inside the body of the orthotic device. The second sensor may be configured to generate a second electric power signal in response to flexing applied by the user's foot in the second area.

At block 806, a control unit may be disposed in a third area inside the body of the orthotic device.

At block 808, the first and second sensors may be communicatively coupled with the control unit, to enable processing of the first and second electric power signals generated by the first and second sensors in response to application of the pressure and flexing to the orthotic device body.

At block 810, a power storage device may be disposed inside the orthotic device body or externally to the device.

At block 812, the power storage device may be communicatively coupled with the control unit, to enable harvesting of the electric charge resulting from the processing of the first and second electric power signals by the control unit.

The embodiments described herein may be further illustrated by the following examples. Example 1 is an orthotic device comprising an orthotic device body; at least two sensors spatially disposed inside the orthotic device body, a first of the at least two sensors to provide a first output responsive to pressure resulting from application of mechanical force to the orthotic device body, a second of the at least two sensors to provide a second output responsive to flexing resulting from the application of mechanical force to the orthotic device body; and a control unit communicatively coupled with the at least two sensors inside the orthotic device body to receive and process the first and second outputs provided by the at least two sensors in response pressure and flexing resulting from the application of mechanical force to the orthotic device body.

Example 2 may include the subject matter of Example 1, and further specifies that at least two sensors are to sense mechanical force applied to the orthotic device body by a user's foot substantially placed on the orthotic device body.

Example 3 may include the subject matter of Example 1, and further specifies that at least two sensors comprise one or more flexible piezoelectric devices.

Example 4 may include the subject matter of Example 3, and further specifies that the first of the at least two sensors is to generate a first electric power signal in response to the pressure to provide the first output.

Example 5 may include the subject matter of Example 4, and further specifies that the second of the at least two sensors is to generate a second electric power signal in response to the flexing to provide the second output.

Example 6 may include the subject matter of Example 5, and further specifies that the control unit is to extract electric power from the first and second electric power signals for electrical power harvesting to process the first and second outputs.

Example 7 may include the subject matter of Example 6, and further specifies that the device further comprises a power storage device coupled with the control unit, to harvest the extracted electric power.

Example 8 may include the subject matter of Example 7, and further specifies that the power storage device comprises one of a battery disposed inside the orthotic device body and coupled with the control unit via a wired connection, or an external power storage device disposed outside the orthotic device body and coupled with the control unit via a wireless or wired connection.

Example 9 may include the subject matter of Example 8, and further specifies that the battery is disposed in an area of the orthotic device body that corresponds to an arch area of a user's foot.

Example 10 may include the subject matter of Example 1, and further specifies that at least two sensors comprise capacitor devices, wherein the first of the at least two sensors comprises a capacitor with a deformable dielectric that is responsive to the pressure.

Example 11 may include the subject matter of Example 10, and further specifies that the second of the at least two sensors comprises an inter-digitated capacitor with compressible dielectric that is responsive to the flexing.

Example 12 may include the subject matter of Example 1, and further specifies that at least one of the first and second sensors and the control unit are disposed inside the orthotic device body in a flexible printed circuit board (PCB) former.

Example 13 may include the subject matter of Example 1, and further specifies that the first sensor is placed in a first area of the orthotic device body that corresponds to a ball area or a heel area of a user's foot.

Example 14 may include the subject matter of Example 1, and further specifies that the second sensor is placed in a second area of the orthotic device body that corresponds to a rear of a ball area of a user's foot.

Example 15 may include the subject matter of Example 1, and further specifies that the device further comprises an analog-to-digital converter (ADC) coupled with the first and second sensors to convert the first and second outputs from an analog format to a digital format for the control unit.

Example 16 may include the subject matter of Example 15, and further specifies that the control unit is to provide processed outputs to a computing device external to the orthotic device.

Example 17 may include the subject matter of Example 15, and further specifies that the device further comprises a transceiver to transmit the processed outputs to the external computing device.

Example 18 may include the subject matter of Examples 1 to 17, and further specifies that the orthotic device is incorporated in an article of footwear, wherein the orthotic device is insertable or embeddable in the article of footwear.

Example 19 is an article of footwear, comprising an orthotic device, having: an orthotic device body; at least two sensors spatially disposed inside the orthotic device body, a first of the at least two sensors to provide a first output responsive to pressure resulting from application of mechanical force to the orthotic device body, a second of the at least two sensors to provide a second output responsive to flexing resulting from the application of mechanical force to the orthotic device body; and a control unit communicatively coupled with the at least two sensors inside the orthotic device body to receive and process the first and second outputs provided by the at least two sensors in response pressure and flexing resulting from the application of mechanical force to the orthotic device body, wherein to process includes to extract electric power from the first and second outputs and to provide the extracted electric power for electrical power harvesting.

Example 20 may include the subject matter of Example 19, and further specifies that the first of the at least two sensors is to generate a first electric power signal in response to the pressure to provide the first output, wherein the second of the at least two sensors is to generate a second electric power signal in response to the flexing to provide the second output, and wherein the first and second sensors comprise piezoelectric devices.

Example 21 is a method for providing an orthotic device, comprising: first disposing a first sensor in a first area inside a body of an orthotic device, the first sensor to generate a first electric power signal in response to pressure applied by a user's foot to the first area, second disposing a second sensor in a second area inside the body of the orthotic device, the second sensor to generate a second electric power signal in response to flexing applied by the user's foot in the second area; third disposing a control unit in a third area inside the body of the orthotic device; and communicatively coupling the first and second sensors with the control unit, to enable processing of the first and second electric power signals generated by the first and second sensors in response to application of the pressure and flexing to the orthotic device body.

Example 22 may include the subject matter of Example 21, and further specifies that the method further comprises: disposing a power storage device inside the orthotic device body or externally to the orthotic device; and communicatively coupling the power storage device with the control unit, to enable harvesting of electric charge resulting from the processing of the first and second electric power signals by the control unit.

Example 23 may include the subject matter of Example 21, and further specifies that the method further comprises: communicatively coupling a transceiver with the control unit inside the orthotic device body; providing a power storage device that is external to the orthotic device; and communicatively coupling the power storage device with the control unit via the transceiver, to enable harvesting of electric charge resulting from the processing of the first and second electric signals by the control unit.

Example 24 may include the subject matter of Example 21, and further specifies that the first, second, and third disposing include placing at least some of the first and second sensors and the control unit in a flexible printed circuit board (PCB) former.

Example 25 may include the subject matter of Examples 21 to 24, and further specifies that the first disposing of a first sensor in a first area comprises first disposing a first sensor in the first area that corresponds to at least one of a heel of a user's foot or a ball of the user's foot, second disposing of a second sensor in a second area comprises second disposing a second sensor in the second area that corresponds to a rear of the ball of the user's foot, and third disposing a control unit in a third area comprises disposing the control unit in the third area that corresponds to an arch area of the user's foot.

Various operations are described as multiple discrete operations in turn, in a manner that is most helpful in understanding the claimed subject matter. However, the order of description should not be construed as to imply that these operations are necessarily order dependent. Embodiments of the present disclosure may be implemented into a system using any suitable hardware and/or software to configure as desired.

Although certain embodiments have been illustrated and described herein for purposes of description, a wide variety of alternate and/or equivalent embodiments or implementations calculated to achieve the same purposes may be substituted for the embodiments shown and described without departing from the scope of the present disclosure. This application is intended to cover any adaptations or variations of the embodiments discussed herein. Therefore, it is manifestly intended that embodiments described herein be limited only by the claims and the equivalents thereof.

What is claimed is:

1. An orthotic device, comprising:
   an orthotic device body;
   a flexible printed circuit board (PCB) former disposed inside the orthotic device body;
   at least two sensors spatially disposed inside the orthotic device body and disposed on the flexible PCB former, a first of the at least two sensors to provide a first output responsive to pressure resulting from application of mechanical force to the orthotic device body, a second of the at least two sensors to provide a second output responsive to flexing resulting from the application of mechanical force to the orthotic device body;
   a control unit disposed on the flexible PCB former and communicatively coupled with the at least two sensors inside the orthotic device body to receive and process the first and second outputs provided by the at least two sensors in response to pressure and flexing resulting from the application of mechanical force to the orthotic device body, wherein to process includes to extract electric power from the first and second outputs for electric power harvesting; and
   a power storage device coupled with the control unit via a flexible connector, wherein the control unit is to provide the extracted electric power to the power storage device via the flexible connector, to harvest the electric power.

2. The orthotic device of claim 1, wherein the at least two sensors are to sense mechanical force applied to the orthotic device body by a user's foot substantially placed on the orthotic device body.

3. The orthotic device of claim 1, wherein the at least two sensors comprise one or more flexible piezoelectric devices.

4. The orthotic device of claim 3, wherein the first of the at least two sensors is to generate a first electric power signal in response to the pressure to provide the first output.

5. The orthotic device of claim 4, wherein the second of the at least two sensors is to generate a second electric power signal in response to the flexing to provide the second output.

6. The orthotic device of claim 1, wherein the power storage device comprises a battery disposed inside the orthotic device body and coupled with the control unit via a wired connection provided by the flexible connector.

7. The orthotic device of claim 6, wherein the battery is disposed in an area of the orthotic device body that corresponds to an arch area of a user's foot.

8. The orthotic device of claim 1, wherein the at least two sensors comprise capacitor devices, wherein the first of the at least two sensors comprises a capacitor with a deformable dielectric that is responsive to the pressure.

9. The orthotic device of claim 8, wherein the second of the at least two sensors comprises an inter-digitated capacitor with a compressible dielectric that is responsive to the flexing.

10. The orthotic device of claim 1, wherein the first sensor is placed in a first area of the orthotic device body that corresponds to a ball area or a heel area of a user's foot.

11. The orthotic device of claim 1, wherein the second sensor is placed in a second area of the orthotic device body that corresponds to a rear of a ball area of a user's foot.

12. The orthotic device of claim 1, further comprising an analog-to-digital converter (ADC) coupled with the first and second sensors to convert the first and second outputs from an analog format to a digital format for the control unit.

13. The orthotic device of claim 12, wherein the control unit is to provide processed outputs to a computing device external to the orthotic device.

14. The orthotic device of claim 13, further comprising a transceiver to transmit the processed outputs to the external computing device.

15. The orthotic device of claim 1, wherein the orthotic device is incorporated in an article of footwear, wherein the orthotic device is insertable or embeddable in the article of footwear.

16. An article of footwear, comprising:
an orthotic device, having:
an orthotic device body with a flexible printed circuit board (PCB) former disposed inside the orthotic device body;
at least two sensors spatially disposed inside the orthotic device body and disposed on the flexible PCB former, a first of the at least two sensors to provide a first output responsive to pressure resulting from application of mechanical force to the orthotic device body, a second of the at least two sensors to provide a second output responsive to flexing resulting from the application of mechanical force to the orthotic device body;
a control unit disposed on the flexible PCB former and communicatively coupled with the at least two sensors inside the orthotic device body to receive and process the first and second outputs provided by the at least two sensors in response to pressure and flexing resulting from the application of mechanical force to the orthotic device body, wherein to process includes to extract electric power from the first and second outputs and to provide the extracted electric power for electrical power harvesting; and
a power storage device coupled with the control unit via a flexible connector, wherein the control unit is to provide the extracted electric power to the power storage device via the flexible connector, to harvest the electric power.

17. The article of footwear of claim 16, wherein the first of the at least two sensors is to generate a first electric power signal in response to the pressure to provide the first output, wherein the second of the at least two sensors is to generate a second electric power signal in response to the flexing to provide the second output, and wherein the first and second sensors comprise piezoelectric devices.

18. A method, comprising:
disposing a first sensor in a first area inside a body of an orthotic device to be disposed on a flexible printed circuit board (PCB) former, the first sensor to generate a first electric power signal in response to pressure applied by a user's foot to the first area,
disposing a second sensor in a second area inside the body of the orthotic device to be disposed on the flexible PCB former, the second sensor to generate a second electric power signal in response to flexing applied by the user's foot in the second area;
disposing a control unit in a third area inside the body of the orthotic device on the flexible PCB former;
communicatively coupling the first and second sensors with the control unit, to enable processing of the first and second electric power signals generated by the first and second sensors in response to application of the pressure and flexing to the orthotic device body, wherein processing includes extracting electric power from first and second outputs for electric power harvesting;
disposing a power storage device inside the orthotic device body; and
coupling the power storage device with the control unit with a flexible connector, to provide the extracted electric power to the power storage device via the flexible connector, to harvest the electric power.

19. The method of claim 18, further comprising:
communicatively coupling a transceiver with the control unit inside the orthotic device body, to provide the first and second electric power signals to an external device.

20. The method of claim 18, wherein disposing of a first sensor in a first area comprises disposing a first sensor in the first area that corresponds to at least one of a heel of a user's foot or a ball of the user's foot, disposing of a second sensor in a second area comprises disposing a second sensor in the second area that corresponds to a rear of the ball of the user's foot, and disposing a control unit in a third area comprises disposing the control unit in the third area that corresponds to an arch area of the user's foot.

* * * * *